United States Patent [19]

Boute et al.

[11] Patent Number: 4,601,291
[45] Date of Patent: Jul. 22, 1986

[54] BIOMEDICAL SYSTEM WITH IMPROVED MARKER CHANNEL MEANS AND METHOD

[75] Inventors: Willem Boute, Doesburg; Guus Stoop; Gerrit W. van Arragon, both of Dieren; Kornelis A. Mensink, Brummen, all of Netherlands

[73] Assignee: Vitafin N.V., Curacao, Netherlands Antilles

[21] Appl. No.: 596,916

[22] Filed: Apr. 5, 1984

[30] Foreign Application Priority Data

Feb. 10, 1984 [EP] European Pat. Off. ............ 84101388

[51] Int. Cl.<sup>4</sup> ............................................. A61N 1/36
[52] U.S. Cl. .............................. 128/419 PT; 128/697; 128/710
[58] Field of Search ................. 128/419 PT, 697, 710, 128/711, 731

[56] References Cited

U.S. PATENT DOCUMENTS

| | | | |
|---|---|---|---|
| 3,742,938 | 7/1973 | Stern | 128/697 |
| 3,946,744 | 3/1976 | Averbach | 128/419 PT |
| 4,172,459 | 10/1979 | Hepp | 128/697 |
| 4,188,956 | 2/1980 | John | 128/731 |
| 4,323,074 | 4/1982 | Nelms | 128/419 PG |
| 4,339,800 | 7/1982 | Woods | 364/417 |
| 4,374,382 | 2/1983 | Markowitz | 128/419 PT |

FOREIGN PATENT DOCUMENTS 0011935 6/1980 European Pat. Off. .
0080821 11/1982 European Pat. Off. .

OTHER PUBLICATIONS

"Pacemaker Diagnostic Diagrams" PACE, vol. 8, Sep.-Oct. 1985, pp. 691-700.
"Notation System and Overlay Diagrams for the Analysis of Paced Electrocardiograms"; PACE, vol. 6, Jan.-Feb. 1983; pp. 73-80.
"Initial Experience with Universal Pacemakers"; PACE, vol. 6; Jul.-Aug. 1983; pp. 806-810.
"Timing Markers Showing Pacemaker Behavior to Aid in the Follow-Up of a Physiological Pacemaker", PACE, vol. 6, Jul.-Aug. 1983, pp. 801-805.
"Interpretation of Dual Chamber Pacemaker Electrocardiograms", PACE, vol. 8, pp. 6-16.

Primary Examiner—William E. Kamm
Attorney, Agent, or Firm—Woodcock Washburn Kurtz Mackiewicz & Norris

[57] ABSTRACT

A biomedical system such as a pacemaker system having an implantable pacemaker and external apparatus, with communications capability for communicating between the implanted device and the external apparatus, characterized by the implanted device having means for cyclically transmitting event and device timing data representative of each prior device interval, the external apparatus having means for receiving and storing the data and for graphically constructing a graphic output representative of the timing and event information over a plurality of device cycles. Graphic output preferably includes a linear timing graph representative of timing functions of the implanted device.

23 Claims, 10 Drawing Figures

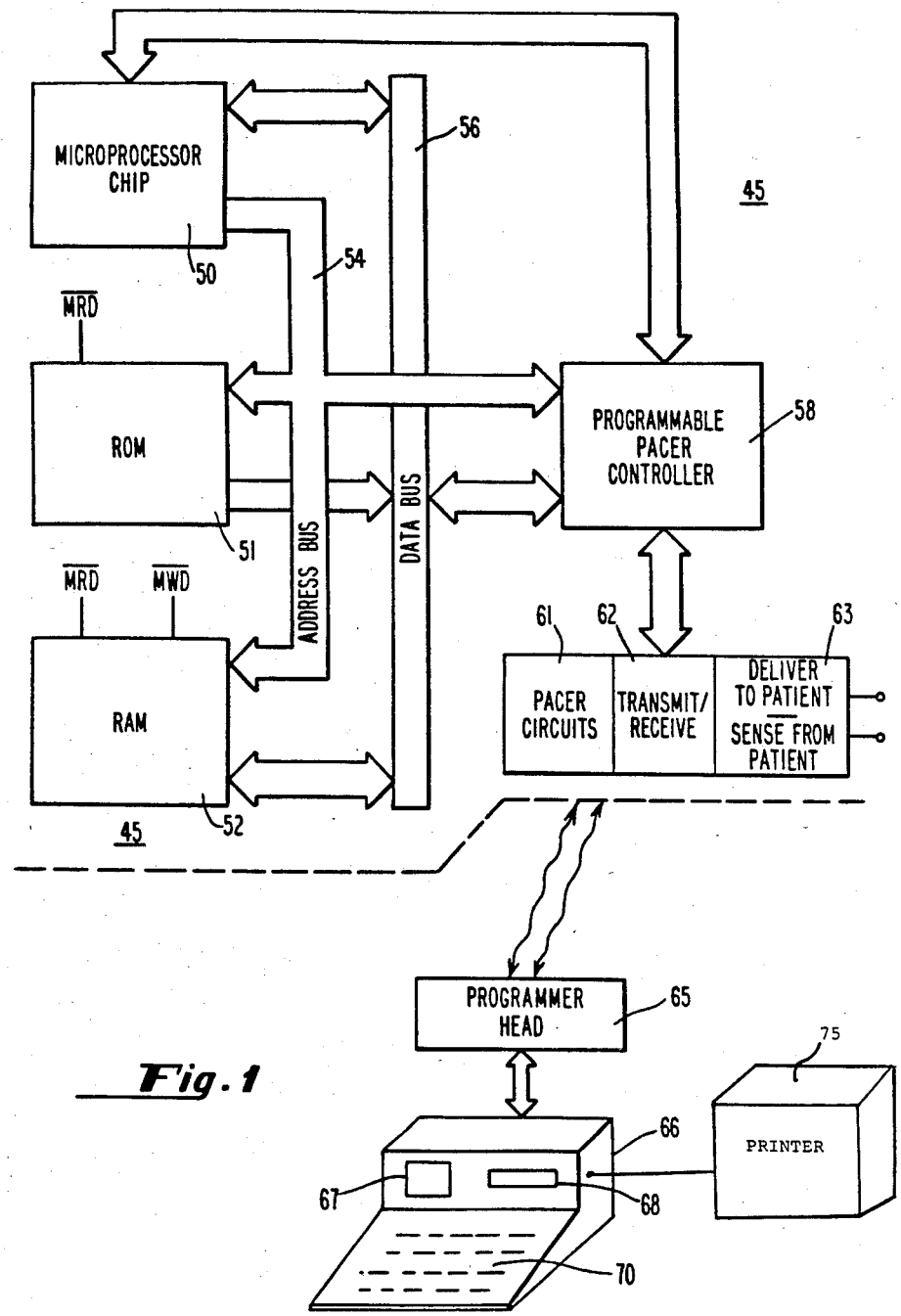

BIOMEDICAL SYSTEM WITH IMPROVED MARKER CHANNEL MEANS AND METHOD

BACKGROUND OF THE INVENTION

1. Field of the Invention

This invention relates to biomedical systems for communicating with implanted devices such as cardiac pacemakers, muscle stimulators, drug dispensers and the like and, in particular, systems which have the capacity for providing a display of event and timing data transmitted from the implanted device.

2. Background of the Prior Art

With the increased use of programmable biomedical systems, and in particular cardiac pacing systems having an implantable pacemaker device and external programmer apparatus, there has developed an awareness of the importance of providing useful information concerning the operation of the implanted device. For example, in cardiac pacing systems, an ECG alone does not provide the doctor with the desired information, whether the ECG is obtained internally by the pacemaker or externally. There is a lot of information which can be obtained by the implanted pacemaker and transmitted for external output, which supplements the ECG information and enables the doctor to determine whether the pacemaker is operating properly, whether the selected mode is optimum, etc. Prior art biomedical systems utilizing implantable devices are known, wherein sensed diagnostic data or patient data that has been generated by the implantable device is transmitted out to external apparatus for display or other indication. For example, in the pacemaker area, it is known to have a separate analog channel for transmission of real time QRS data, the analog transmission channel being separate from and additional to the communications channel for operator programming and interrogation. While, of course, plural or even multiple channels can be used if there is no limit on expense or power requirements, there is a great need for efficient use of a single communications channel, which is capable of handling both the normal programming and interrogation requirements, as well as outputting patient and other diagnostic data.

State of the art pacemaker systems have provided for what is referred to as marker channel information which is printed in relation to an ECG so as to provide supplemental information. For example, events such as pacing or sensing of a natural heartbeat are recorded with a mark indicating the time of the event relative to the ECG. This is helpful to the physician in interpreting the ECG. Existing sytems which provide a marker channel output operate basically by outputting the pacemaker event, e.g. a delivered stimulus or sensed natural heartbeat, at about the time of the event, thereby inherently providing the timing of the event in relation to the recorded ECG. However, this arrangement places limitations upon the system capacity to output and record information concerning the wide range of events that can occur each pacing cycle, as well as desired timing information relating to the pacer operation. The requirement of continuously transmitting to the external apparatus at the time of each event or timed out interval requires a substantial amount of extra control capacity within a pacemaker, in order not to interfere with the ongoing pacemaker functioning. Thus prior art pacing systems have generally been limited to communicating simple event data, for the practical reasons of limiting the amount of circuitry which is dedicated for handling the data transmissions. This limitation is undesirable, particularly for dual chamber pacing systems, where it is desirable to provide marker channel displays for events and pacemaker timing corresponding to both the atrial and ventricular chambers. There thus exists a substantial need in the art to overcome the practical difficulties associated with real time communication, and to provide more informative and readable marker channel displays.

Applicant refers to U.S. application Ser. No. 465,891, titled "Biomedical System With Improved Means And Method For Communicating With Implanted Device", assigned to the same assignee, which is incorporated by reference. This application contains a disclosure of techniques of communication between the external programming device and the pacemaker as used in the system of the assignee of this invention, which communications arrangement forms a part of the environment of this invention. Reference is made to this application as well as to other published patent literature, for teachings as to specifics of communications methods and means employed in pacing systems, whereby data is collected by a pacemaker and transmitted from the implanted pacemaker to an external programmer device, where the data can be presented in different visual forms. The well known techniques utilized in the pacemaker industry for transmitting data from an implanted pacemaker to an external control apparatus, and vice versa, are understood to be part of the background of this invention, but as such do not form any portion of the novel features thereof.

SUMMARY OF THE INVENTION

It is an object of this invention to provide a biomedical system having an implanted device and external apparatus for communicating with such device, having means for improved transmission of event and timing data from the implanted device to the external apparatus.

It is another object of this invention to provide improved communication between an implanted pacemaker device and external apparatus, the external apparatus having means for generating an improved marker channel display.

It is another object of this invention to provide a pacing system comprising an implantable dual chamber cardiac pacemaker the system having means for two way communication between the implanted pacemaker and external apparatus, the system further having improved means for presenting a display of both atrial and ventricular event and timing data.

It is another object of this invention to provide a pacemaker system with means and method of presenting an improved graphic display of pacemaker data on a cyclical basis.

It is another object of this invention to provide a communication system and method for communicating with an implantable device such as a cardiac pacemaker, the pacemaker or like device operating on a cyclic basis, with an improved communication mode for outputting data from the device for display and operator observation.

It is another object of this invention to provide an implantable pacemaker system, having a simple and reliable communications channel adapted to be used for device programming and interrogation, and for outputting patient and device data, the system further having means for external storage of data corresponding to a predetermined plurality of pacemaker cycles, whereby a graphic presentation of said data can be produced upon operator command.

In view of the above objects, there is provided a biomedical system, and in particular a cardiac pacing system, with improved means and method for providing a marker channel display of event and timing information transmitted from an implanted pacemaker. In a preferred embodiment, the system is a dual chamber pacemaker system, and provides a graphic output of both atrial and ventricular information, the information comprising both event data and pacemaker timing data which is presented in a linear format. System reliability and capacity is enhanced by accumulating data each pacer cycle, or interval, and transmitting a batch of data for the just ended interval during the next succeeding interval. The external apparatus of this system comprises software means for controlling two-channel printing of graphics representing timing and event data for the atrium and ventricle respectively.

BRIEF DESCRIPTION OF THE DRAWINGS

FIG. 1 is a block diagram showing, for the illustrative embodiment of a cardiac pacing system, an implanted programmable pacer and external apparatus comprising a programmer head and computer input/output apparatus.

DESCRIPTION OF THE PREFERRED EMBODIMENTS

Figure 2A:
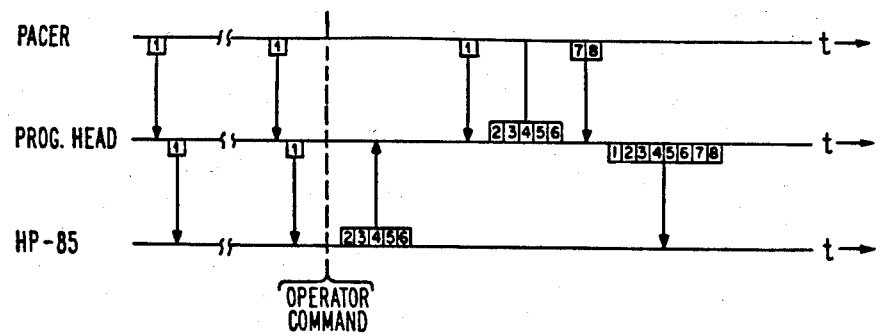
FIG. 2A is a diagram illustrating a format of information flow for a cardiac pacemaker system, the flow being between an implanted pacemaker, programmer head and computer.

Referring now to FIG. 1, there is shown a block diagram of the primary components of an implantable pacemaker 45, which is exemplary of the implantable device of the system of this invention. Shown in block 50 is a microprocessor chip, and as used hereinafter the term microprocessor or microprocessor element means a commercially available microprocessor, whether of one or more chips. A preferred microprocessor for use in the application of this invention as part of a programmable cardiac pacer or other implantable device is the CDP 1802 microprocessor made by RCA. Other CMOS microprocessors are available for use in this invention, e.g. the Hitachi 8080A. The CDP 1802, hereinafter the 1802, is fabricated on a single chip utilizing a silicon gate CMOS structure. Because of its CMOS structure it offers the design advantages of wide operating temperature range, relatively high speed, high noise immunity and in particular low power consumption. It is to be understood that particularly for an implantable pacer application, where the lifetime of the battery source is important, the low power CMOS microprocessor is particularly advantageous. Descriptions and specifications of the CDP 1802 and other equivalent microprocessors are freely available and in the technical literature.

Still referring to FIG. 1, an address bus 54 is shown interconnected with ROM memory 51, RAM memory 52, and the programmable pacer controller circuit 58. The ROM is suitably an RCA model CPD 1833 while the RAM is suitably an RCA model CDP 1822 chip. ROM and RAM are used to store, for example, pacer routines; permanent and temporary parameter data; acquired diagnostic data; and pacemaker data, including model data. The model data can be inputed at the factory, or later, and corresponds to the permanent programming of the device. The data bus 56 interconnects the microprocessor chip 50 with ROM 51, RAM 52 and pacer controller 58. Reference is made to co-pending EP-application Ser. No. 81108939.0, which describes additional detail of controller block 58, and which is incorporated by reference. Although only one ROM and one RAM block are shown, it is to be understood that there is no limitation on the amount of memory subject only to practical design considerations.

Connected to the programmable pacer controller 58 are circuits 61, 62 and 63. As is illustrated, data can pass either way between each of these circuits and controller 58. Pacer circuits 61 comprise conventional logic and pulse generation circuits, as are found in conventional pacemakers of the single or dual chamber types. Such circuits, to the extent that they are needed in addition to the microprocessor circuitry, are standard circuits available in the art. Block 62 represents transmit/receive circuitry, which may comprise conventional circuitry for transmitting digital data to the external apparatus, and for receiving program and interrogation data back from the external apparatus. This circuitry includes a modem, as is known in the art. Similarly, block 63 contains conventional circuitry for interfacing with the patient. For example, block 63 may contain stimulus output pulse forming and amplifying circuitry, amplifier circuitry for amplifying sensed cardiac signals, etc. It is seen that two output terminals are shown, illustrating that the pacer may be either a single chamber or a dual chamber pacemaker.

Programmer head 65 is shown in communication with transmit/receive block 62 of the pacer 45. The programmer head 65 may be of any conventional form as utilized in the industry, adapted for positioning on or about the patient's chest or otherwise in proximity to the implanted pacemaker, for communicating therewith. In a standard embodiment, the programmer head contains a magnet or magnet means, the presence of which is sensed by the pacemaker, for initiating transmission of identification ("ident") signals from the implanted pacemaker to the programmer head. Programmer head 65 also contains suitable conventional means for transmitting and receiving electromagnetic data signals to and from the pacer.

Programmer head 65, may be a stand-alone unit, or may be connected by suitable cable means directly to a computer device illustrated at 66, which in the preferred embodiment is an HP-85 computer or equivalent. As illustrated, there is a keyboard 70, tape input 68, and display 67, the display suitably being a video display as illustrated, and/or printed or graphical copy means. The device 66 may be connected to drive a separate printer 75, as shown. The operator communicates with the system by inputting data through the keyboard, and by placing a tape cartridge at input 68. The HP-85 is a well known commercially available device, the operational capabilities and capacity of which are known to the public. It is to be noted that other forms of computer devices may be used in an equivalent manner. Such a computer device has, of course, its own internal memory for holding data inputted through the keyboard or through tape, or for holding data that has been transmitted to it from the pacemaker and through the programmer head.

Referring now to FIG. 2A, there is shown a timing diagram illustrating transmission of data between the pacer, programmer head and HP-85 computer. Without the programmer head being placed in proximity to the pacer, nothing is transmitted from the pacer. However, when the pacer senses the programmer head magnetic field, or any equivalent turn-on signal, it commences to transmit an ident byte once each pacer cycle. In FIG. 2A, this is illustrated by the numeral 1, the ident byte being transmitted from the pacer to the program head, and in turn from the program head to the HP-85. The ident byte establishes basic timing, i.e. it synchronizes transmission, and also carries basic information, including relevant data from the prior pacer cycle. By way of example, the ident byte for applicant's DPG pacemaker is as follows:

Bit 1—end of life software, yes or no
Bit 2—end of life hardware, yes or no
Bit 3—pacer locked or unlocked
Bit 4—V signal sensed, yes or no
Bit 5—A signal sensed, yes or no
Bit 6-8—number of bytes needed from transmitter for interrogation or programming, i.e., information concerning format.

In a normal operating mode, the format has an 8 byte sequence per cycle, when the operator has inputted an instruction which is to be sent from the programmer head to the pacer. The sequence, which is illustrated in FIG. 2A, is as follows:
Pacemaker: Identification Byte (1)
Programmer: Instruction Byte (2)
Programmer: Parameter Byte (3)
Programmer: Parameter Byte (4)
Programmer: Data Byte (5)
Programmer: Data Byte (6)
Pacemaker: Data Byte (7)
Pacemaker: Data Byte (8)

The instruction byte, which is generated by the programmer (HP-85) instructs the pacer about the use of following parameter and data information. Bits 4-6 of the instruction byte may be used to indicate the fact that a number of parameters and data are linked, such that only after all linked parameters and data are transferred to the pacer, programming is actually enabled and accomplished. The two parameter bytes are a low order byte (LOB) and high order byte (HOB), constituting a 16 byte address for storing or retrieving data. The two following data bytes provide the data to be stored in the address designated by the parameter bytes, and are dummies if the instruction is an interrogation. The two data bytes that are received back from the pacemaker, being bytes 7 and 8 as illustrated in FIG. 2A, represent data that had been generated in the pacemaker and stored for possible interrogation by the physician, or other response data.

Referring again to FIG. 2A, when the operator inputs a command, or an instruction, bytes 2-6 are transferred from the HP-85 to the program head. Nothing happens until the next ident byte (1) is received in the program head from the pacer. Following this, bytes 2-6 are transferred from the program head to the pacer, the pacer in turn sending back data bytes 7, 8. To end the sequence, all 8 bytes, including the ident byte, the 5 instruction bytes, and the two data bytes from the pacer, are transmitted to the computer. This format, or sequence, which can be carried out each cycle, permits integrity of communication, since the computer can check all of the information that was transmitted during the sequence.

Figure 2B:
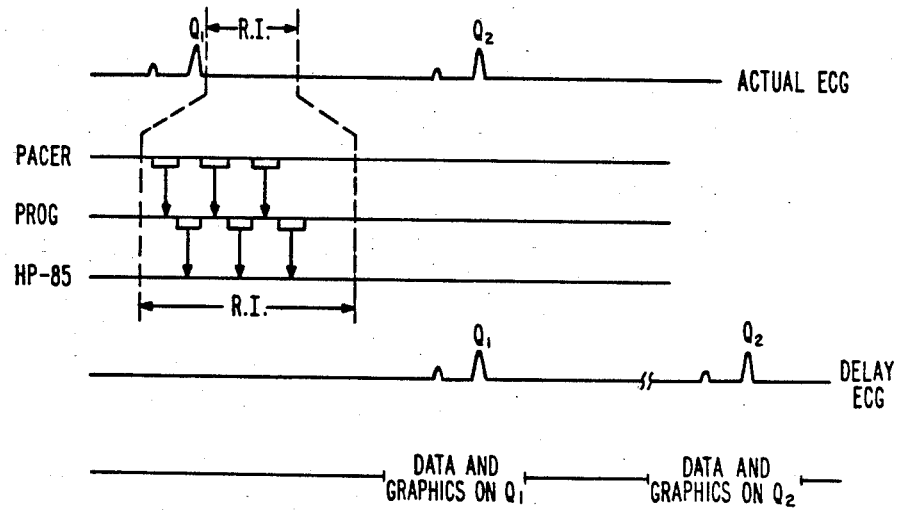
FIG. 2B is a series of timing diagrams, illustrating cyclic transfer of data corresponding to patient ECG from an implanted pacemaker to an external device, and display of the ECG data.

Referring now to FIG. 2B, there is shown a set of timing diagrams illustrating a special communications mode, which mode can be initiated by transmission of a specific instruction to the pacemaker. FIG. 2B shows use of the mode for providing intracardial ECG data from the pacer to the computer, for display to the operator. On the top line, there is shown a timing diagram of the actual ECG of the patient. The first QRS signal illustrated, marked Q1, is sensed by the pacemaker. Following the QRS event, and during the following refractory interval (R.I.), the value of which is a programmable value, the pacer sends out a series of bytes which are received by the programmer and are relayed in turn to the HP-85. The first of a series of bytes is the ident signal, and the following successive bytes contain data descriptive of the QRS which has just been sensed by the pacer. The plural bytes are transmitted from the pacer to the external device in batch form, permitting delayed generation of graphics for each pacer cycle. Thus, in this first illustrative case, the ECG, or graphics relating to the QRS, is printed with a delay of one cycle as compared to the actual ECG. More broadly, the invention comprises storing specified data during a pacer cycle, and transmitting a group of data bytes during the next cycle, for display or storage. Thus, while the pacer is collecting data for cycle n+1, the external apparatus is receiving, and is capable of presenting, data for cycle n. The data can be printed on a delayed cyclical basis, or can be stored and displayed upon operator command. The above reference to U.S. application Ser. No. 465,891 includes additional disclosure of the software steps taken in the pacemaker during communication with the external apparatus.

Figure 3:
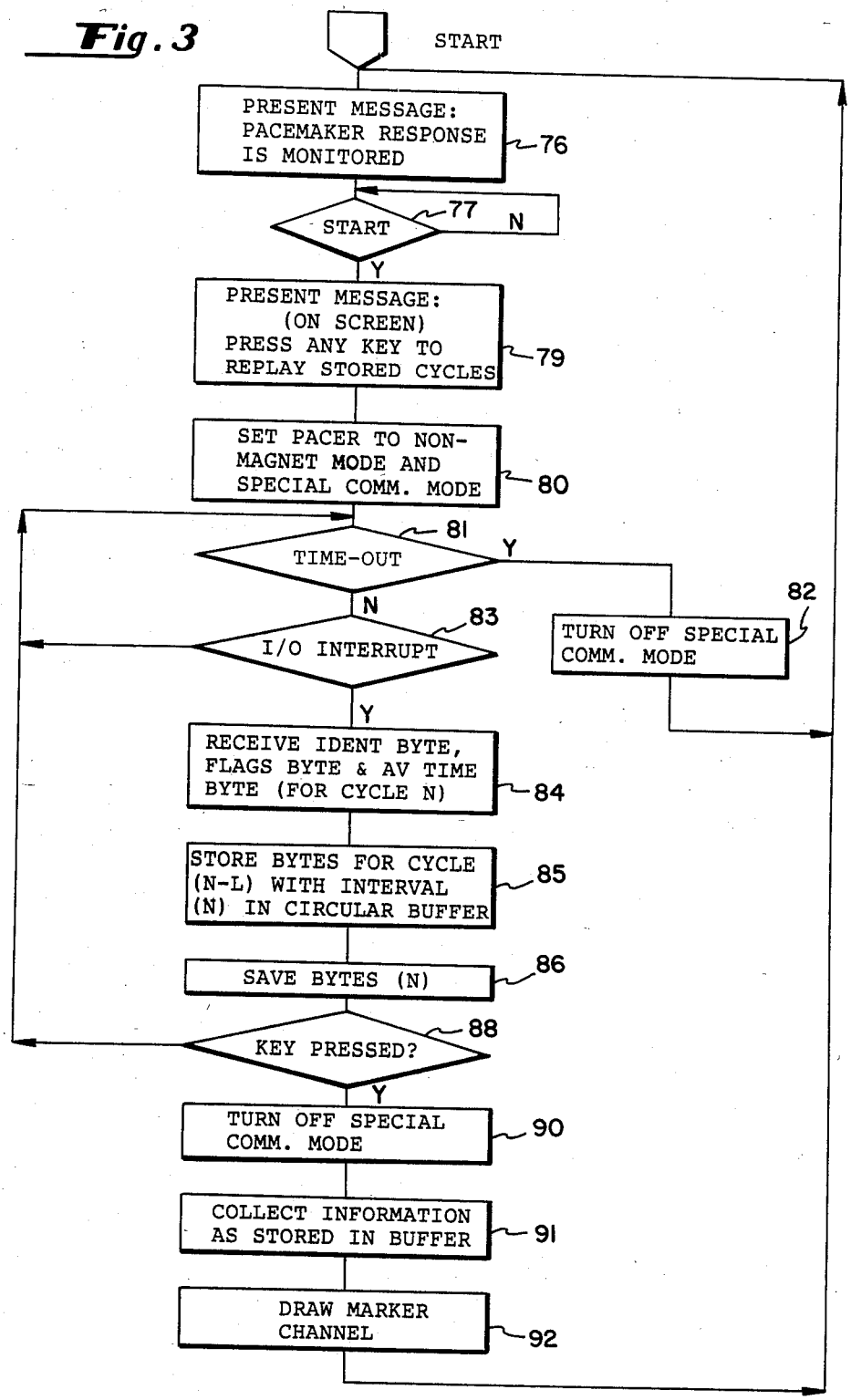
FIG. 3 is a flow diagram illustrating steps taken in the external device of this system to receive and store pacemaker data for printing of the marker channel displays.

Reference is now made to specific software for carrying out the marker channel method of this invention. The preferred embodiment is for a dual channel pacemaker, which forms the example that is illustrated in this specification and in FIGS. 3, 4A, 4B and 5A, B and C. Referring to FIG. 3, there is shown a flow diagram of the steps taken by the external device for acquiring the data necessary to generate the marker channel displays. The routine of FIG. 3 is a routine that is automatically operated when the physician, or operator, selects the marker channel operation, typically in response to a menu that has been presented, as is conventional in the art. It is to be understood that before the start of the routine of FIG. 3, the external device 66, which will be referred to as the "HP" has obtained from the pacemaker two static bytes. These bytes, which can be read from the pacer at anytime before going into the special communications mode required for the channel marker operation, are referred to as the A MODE byte and the V MODE byte. Each of these bytes is an eight bit byte, and they contain the following information:

| A MODE BYTE | | | | | | | |
| --- | --- | --- | --- | --- | --- | --- | --- |
| Enable Wenckebach | | Enable PVC-A trigger | Enable A-A trigger | Enable ASTIM | Enable VVI mode | | Enable Asense |

| V MODE BYTE | | | | | | | |
| --- | --- | --- | --- | --- | --- | --- | --- |
| Enable Non-magnet | Enable DS-V trigger | Enable PVC-V trigger | Enable V-V trigger | Enable VSTIM | Enable Vsense ASTIM | Enable Vsense Asense | Enable PVC-sense |

The A MODE and V MODE bytes represent static data that does not change from cycle to cycle, i.e. it would only be changed when the pacer is re-programmed. For the flow charts that follow, the A MODE and V Mode bytes are assumed to be available in the HP storage, having been generated at the time the pacemaker was last programmed.

When the operator requests the special marker channel operation, the routine of FIG. 3 is entered. First, as indicated at 76 a message appears on the screen, confirming that the pacemaker response is being monitored, i.e., the HP is in communication with the pacemaker. Assuming that the program is started at 77, another message is presented on the screen, as indicated at block 79, telling the operator to press any key when it is desired to replay the last six seconds of the pacer operation. By this it is meant that the marker data for the previous six seconds, or a predetermined number of prior pacer cycles, will be provided. The routine then proceeds at block 80 to set the pacemaker into a non-magnet mode, meaning that it operates in an inhibited mode, and sets the pacemaker into a special communications mode. In this mode, a group of three bytes of information are provided from the pacemaker following each ventricular event, whether a V sense or V stimulus. These three bytes of information, or dynamic bytes, combined with the two static bytes, provide the HP with data to produce the marker graphics. The three dynamic bytes are the ident byte, previously described; a Flags byte; and a byte which provides the AV time for the interval being transmitted. The Flags byte provides information concerning events and/or pacemaker conditions during the last cycle, and is as follows:

| FLAGS BYTE | | | | | | | |
| --- | --- | --- | --- | --- | --- | --- | --- |
| AHR | DS | EAS | Stimul. V | Stimul. A | Wenckewindow | PVold | PVC |

Reference is made to an application assigned to the same assignee, filed in the United States as Ser. No. 566,059 now U.S. Pat. No. 4,554,921. This application discloses details of operation of the assignee's DDD pacemaker, and includes a discussion of the various programmed modes, the automatic Wenckebach or block modes of high rate limit, and other features. This application also teaches the setting of the different flag bits found in Flags byte, and is incorporated herein by reference.

Following setting the pacemaker in the magnet mode and in the special communications mode, at block 81 it is determined whether there has been a time out. There is a time out if the programmer has been removed from the pacer, in which case the HP turns off the special communications mode. Assuming no time out, the HP then next determines at 83 whether an interrupt has been received, i.e. whether an ident byte has been received. When there is an interrupt, the HP receives and stores the three bytes at block 84, which three bytes correspond to cycle (n−1) and are received during cycle (or pacer interval) n. At block 85 the bytes from the prior cycle (n−1) are stored in a circular buffer of a predetermined capacity, such that data for a predetermined number of successive pacer intervals, or cycles can be stored. Thus, at all times during the special communications mode, the HP has available for graphic printout data corresponding to a predetermined number of the most recent pacer intervals. Also at block 85, the HP measures, with its own internal clock, the time from the last prior ident byte to the most recent ident byte, which represents the time of the last pacemaker interval. At block 86 the 3 bytes for cycle (n) are saved, and the process is then repeated until a graphic display is requested.

Figure 4A:
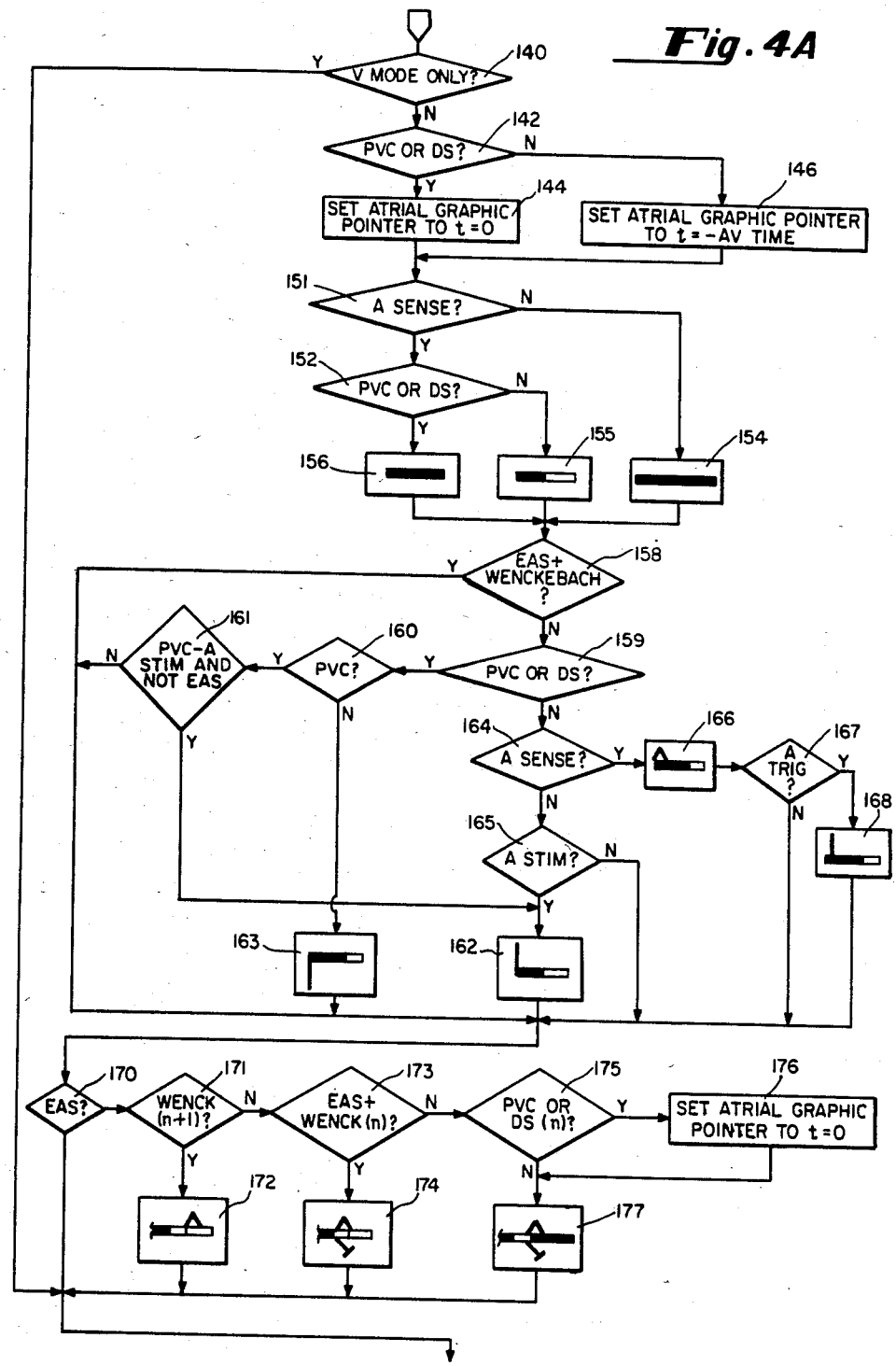
FIGS. 4A AND 4B are a flow diagram illustrating software steps taken by the external device to control printing of the marker channel information.
Figure 4B:
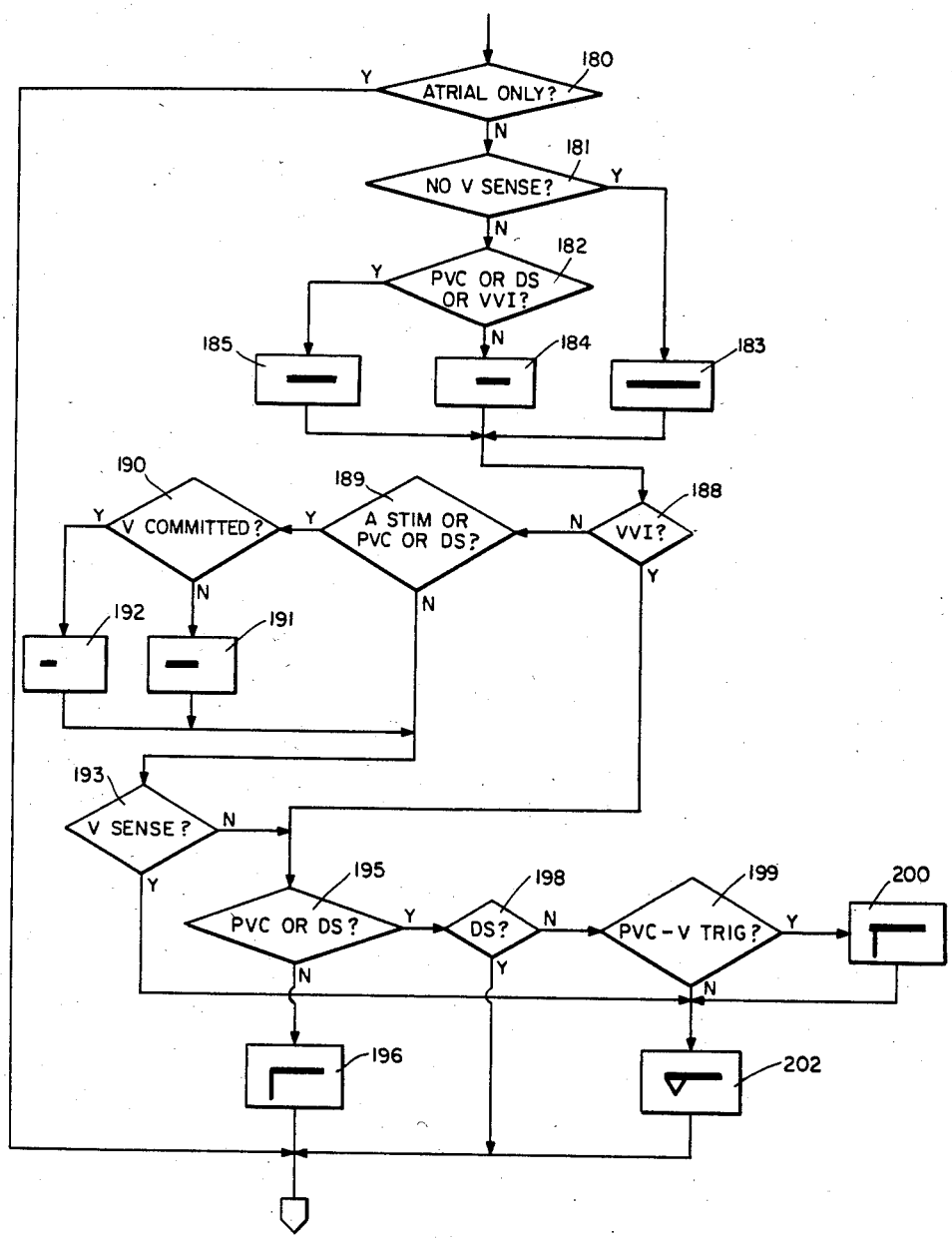

Assuming that the operator has pressed a key, as indicated at 88, the HP then branches so as to control the printer device 75 to print the marker channel graphics. At block 90, the special communications mode is turned off. At block 91, the data corresponding to the last prior predetermined number of pacemaker intervals is collected from the buffer, and then at block 92 the HP controls the actual drawing of the marker channel information. FIGS. 4A and 4B shows the specific steps taken by the HP in doing this.

Figure 5A:
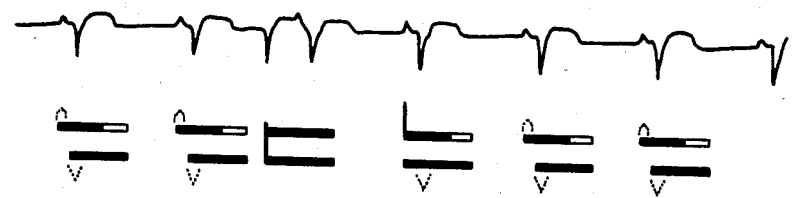
FIGS. 5A, B and C are illustrative marker channel graphs which illustrate different pacemaker events and timing sequences.
Figure 5B:
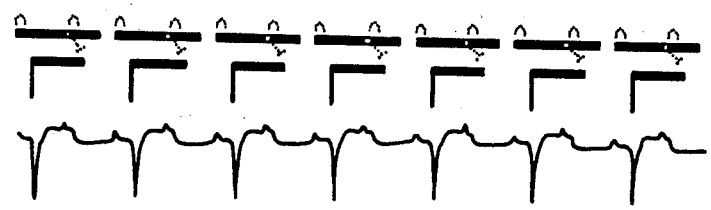
FIG. 5D illustrates the timing of transmission of data bytes from the pacer.
Figure 5C:
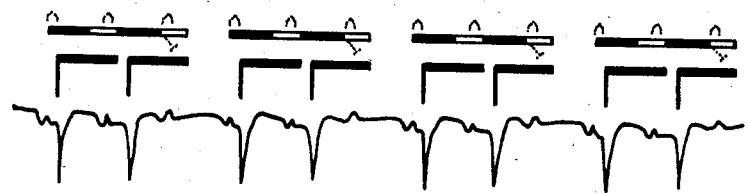
Figure 5D:
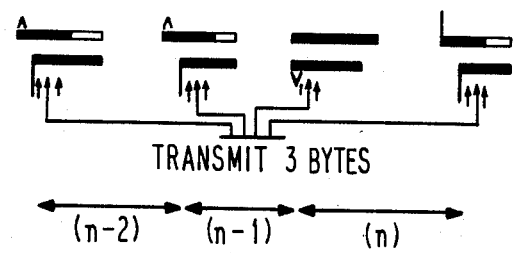

Referring now to FIG. 5D, there are illustrated three consecutive pacemaker cycles. These cycles show the time of sending out the three bytes relative to the end of each cycle, and the relationship of intervals n−2, n−1, and n. As illustrated, an event such as an early atrial sense (EAS) in interval n is communicated in the Flags byte that is transmitted during cycle n+1. Reference is again made to U.S. application Ser. No. 566,059, (U.S. Pat. No. 4,554,921) which provides background information for the discussion that follows.

Referring now to the start of the flow diagram at the top of FIG. 4A, the first determination at block 140 is whether the A Mode byte indicates that there is atrial operation, such that there is an atrial channel to be generated. If this byte indicates that there is no atrial channel, then the program branches to block 180 (FIG. 4B) and examines the V Mode byte. Assuming that there is atrial activity, at block 142 it is determined whether there was, in the prior interval (n−1), a PVC or double sensing (DS). This is done by examining the Flags byte that is transmitted during interval n. Assuming that neither of these events took place, meaning that it was a normal atrial cycle, then the atrial graphic pointer (or the pen that produces the atrial graph) is set to t=−AV time at 146. This is done because the printer normally starts at the ventricular event; thus, when it is an atrial event, the pointer is backed up by AV time, so as to start at the time of the atrial event. Since the AV time has been outputted by the pacer, this information is available. Note that if there was a prior PVC or DS indicated at block 142, then there was no atrial event, and the atrial refractory interval starts exactly at the same time as the ventricular event as indicated at 144. It is next determined at 151 whether, in the programmed mode of operation, A sense is enabled. This is done by examining the appropriate bit of the Flags byte. If no, this means that there is fixed rate atrial pacing, and there is no atrial refractory interval, such that the entire AA interval is drawn at block 154, thus indicating a continuous refractory interval. If A sense is indicated, the program goes to block 152, and again determines whether there had been a PVC or DS. If no, the routine goes to block 155 and draws the refractory interval as a solid line up to the start of the relative refractory interval, and then draws an open line to indicate the extent of the relative refractory interval, which includes the Wenckebach window. If there had been a PVC or DS then the program branches to block 156 and a solid line is drafted for the entire atrial refractory interval.

At the next block 158 the n Flags byte is inspected to determine whether there was an EAS and Wenckebach. If yes, the program skips to block 170. If the answer is no, the program next looks, at block 159, at the Flags byte to determine where there was a PVC or double sense (DS). If yes, the program then inspects the Flags byte again at 160 to determine whether it was a PVC. If it was a PVC, at 161 the A Mode byte is inspected to see if there is an atrial stimulation with a PVC, and the Flags byte is inspected to see if it was not an EAS. If yes, then there is a PVC trigger, and this is drawn at block 162. Otherwise the routine skips to block 170, since there was no double sense and there was no atrial stimulus. Going back a step to block 160, if there was double sensing, then the program goes to block 163 and causes the printing of a verticle line of a length calculated to join the two channels, which is the symbol for double sensing.

Returning to block 159, if there was no PVC or DS, the ident byte is examined at 164 to determine whether there has been an A sense. If no, the Flags byte is inspected at 165 to determine whether the pacer delivered an A stimulus. If yes, at block 162 the stimulus is drawn. If no (as in the case of VDI mode), the routine skips block 162. If there has been an A sense at 164, the symbol for a spontaneous A is generated at 166. Then, at 167, the A Mode byte is inspected to see whether there is to be a triggered atrial stimulus (AAT mode), and if yes the atrial stimulus symbol is added to the spontaneous A symbol at block 168.

Going next to block 170, the program gets the Flags byte from the next cycle (n+1), and determines if there was an EAS (during cycle n). If there was not, then the atrial graphics for the n interval are completed and the routine passes to the ventricular channel portion. If there was, the routine moves to block 171 and examines the n+1 Flags byte to see if the pacer is in Wenckebach mode. If yes, then the symbol for a sensed atrial heart beat during the Wenckebach window of interval n is printed at 172. The A sense symbol is positioned to the right side of the relative refractory interval corresponding to the Wenckebach window. If no, then the flag for the n interval is examined at 173 to see if it indicates that the pacer had been in the Wenckebach mode the cycle before, meaning that the EAS is out of the window and a beat is to be missed. If this is the situation, then the symbol is generated at 174 indicating a sensed EAS and blocking of the Wenckebach delay. Note that this symbol is positioned to the far left of the relative refractory interval, indicating that it was out of the Wenckebach window. If the answer is no, this means that there is no Wenckebach mode and the pacer has gone into 2 to 1 block, requiring that an extended refractory interval was set. This is indicated by drawing an extended horizontal line at block 177. If it is indicated that there was a PVC or DS in the n Flags byte, then the start of the drawing is at t=0, (the time of the ventricular event). The pacer next goes to the ventricular channel portion.

The V Mode byte is first examined at block 180. If it is determined that the V Mode byte indicates that the pacer is in an atrial mode only (AAI, AAT or AAO), then the routine branches to the end. However, if the V Mode byte indicates a V mode, then the program proceeds to block 181 and looks at the last three bits in the V Mode byte to determine whether the pacer is in a mode where there is no ventricular sensing. If so (yes response), as indicated at block 183, the graph pen then draws a continuous ventricular refractory interval, (i.e. no sensing) such that the graph bar is continously solid from interrupt to interrupt. If, at block 181, the answer is no, the program goes to 182 and checks the (n) Flags byte to see whether it is a PVC or DS, or whether the A Mode byte indicates a VVI operation. If it is any of these, then at 185 the pen graphs out a solid line having a duration of the full refractory interval. If none of these is indicated, meaning that it is a dual chamber situation, then the normal ventricular refractory interval is drawn at 184, starting at time O of the ventricular event and lasting for a length which is equal to the atrial interval minus the AV time. This is because the ventricular refractory interval ends at the same time as the atrial refractory interval, but begins AV later.

Next it is determined at 188 from the A Mode byte whether the pacer is in any of the single chamber V modes. If yes, then the routine goes directly to block 195 and determines from the Flags byte whether there is a PVC or DS. Note that for the single chamber case either one of these indicates a normal sensed ventricular pulse (a ventricular sense is designated by the logic of the PVC or DS when in the single chamber ventricular mode). If there has been no sensed ventricular signal, then it was a stimulus, and the pacer draws in the V stimulus symbol at 196. If there is a sensed ventricular signal, the n Flags byte is checked at 198 to see if there was a double sense. If so, the routine exits since the double sense mark has already been generated during the atrial portion of the routine. If no double sense, it is then determined at 199 from the V Mode byte, whether a trigger should be produced in response to a PVC. If yes, the trigger symbol is first generated at 200; then, or if no trigger, the ventricular sense response is generated at 202.

Going back to block 188 where it is determined whether or not there is single mode ventricular operation, if the answer is no, this indicates atrial operation as well. First there is an examination of the n Flags byte at 189 to see if the bits were set for A stim or PVC or DS. If yes, then at block 190 the V Mode byte is examined to see whether or not the ventricular operation is committed, i.e. whether there is an automatic V stimulus or whether V sense is enabled after an A stimulus. If the answer is no, meaning committed, there is no sensing during the AV time, so that the AV interval is drawn in as a solid line at block 191 as part of the refractory interval. If yes (V sense is enabled), a short V blanking period following the A stimulus is drawn in at 192. The routine then goes to examine the ident byte at block 193 and see whether there has been a V sense. If yes, then the V sense symbol is printed at 202; if no, then there has been a V stimulus, and the routine goes to 195 and 196.

Referring now to FIGS. 5A, B and C, there are shown illustrations of the marker channel graphic displays of this invention. Each of the marker channel displays is combined with an ECG recording which is time coincident. It can be seen that the information from the marker channel, along with the ECG, provides very thorough information permitting the physician to interpret and understand the history of the illustrated pacing cycles.

Referring to FIG. 5A, and starting at the left, the two marker channels are shown positioned below the EKG. The upper marker channel starts with a solid line, with the symbol for a detected natural atrial beat positioned above the start of the solid line. The solid line represents the absolute atrial refractory period, being the period during which no A sensing is done. This line terminates in an enclosed linear extension, which indicates the time of the relative atrial refractory period, i.e. the period during which atrial signals can be sensed, but in response to which the pacemaker does not necessarily provide an AV time out. On the lower line, which represents the timing of the ventricular channel, it is seen that the solid bar, representing the ventricular refractory interval, starts a certain time after the beginning of the atrial refractory period, this time being the AV delay. The "V" symbol just below the start of the ventricular refractory interval indicates a sensed ventricular beat. Note that the ventricular refractory interval terminates at the same time as the termination of the relative atrial refractory interval. Thus, after this termination, both the A and V sense are enabled. The next cycle, as illustrated, is the same, but the third cycle is initiated by a double sense. A double sense is defined as the sensing of a beat in both channels, either simultaneously or within a small interval of time, e.g. 10-20 ms. Note that here the event was a PVC, since there was no preceding atrial signal sensed. Following this, and timing out of the refractory intervals, it is seen that the pacer times out a complete A-A interval, and delivers an atrial stimulus pulse. Correspondingly, a blanking period is shown in the ventricular channel, followed by the V symbol, indicating that a ventricular natural beat was sensed within the AV interval. The following intervals as illustrated represent sensing of both atrial and ventricular natural signals. As illustrated, each of the channels, the upper atrial channel and the lower ventricular channel, provide linear timing diagrams, presenting timing information concerning sensing in each channel. An advantage provided by this invention is that there is constant information concerning the sense condition in each channel, i.e., the channel is either in the absolute refractory period; the relative refractory period, or the absolute sense period. By providing this information along with the symbols for the events, as well as the corresponding ECG, the doctor has very thorough information concerning the activity of the patient's heart and the pacemaker. As used herein, the phrase "timing data" or "pacemaker timing data" refers to the linearly presented refractory interval information, which indicates the exact timing of the refractory interval and the absence of a refractory interval, the latter representing the absolute sensing interval; and to the timing of events such as sensed beats and delivered stimulus pulses, blanking, etc. The term event data refers to data concerning the nature of events, both natural and artificial, e.g., sensed and delivered beats, pulse height and duration, capture following delivery of a pulse, etc.

Referring to FIG. 5B, there is shown a marker channel output, combined with an analog ECG drawing, which shows either a VDD or DDD mode of operation, when a sensed high atrial rate has resulted in a 2:1 "block", i.e., one ventricular pulse is delivered every two natural atrial signals. Every other atrial signal is a sensed EAS, but without Wenckebach operation, such that there is no subsequent synchronously generated ventricular stimulus. Further, while the ventricular refractory interval is shown to end at the normal time, the atrial refractory interval is extended, as illustrated.

Referring to FIG. 5C, there is shown an example of a VDD or DDD operation, wherein the Wenckebach mode is effectively causing every third atrial signal to be blocked. Note that for each group of three sensed atrial signals shown on the upper channel, there are two ventricular stimulus signals. The first atrial signal has been sensed during an absolute sensing interval, and the ventricular stimulus is delivered after a programmed AV delay. The next atrial signal is sensed at a time during the Wenckebach window, and it is seen that the ventricular refractory interval times out until the end of the Wenckebach window. Thereafter the AV delay is timed out, and the second ventricular stimulus is delivered, thus effectively extending the AV delay. The next atrial stimulus is sensed during the relative refractory interval, but out of the Wenckebach window, such that it is inhibited from causing a synchronously generated ventricular stimulus. The next natural occuring atrial heartbeat is sensed during the following absolute atrial refractory interval, and the sequence repeats. Again, the presentation of the linear timing data along with the corresponding symbols presents a very clear presentation of what has taken place.

There is thus disclosed a preferred embodiment, comprising a dual chamber pacing system with special communications mode for providing a marker channel graphic output. The marker channel graphics of this invention provide event data in combination with linear pacemaker timing data, the combination providing the physician with increased ability to interpret the patient ECG and pacemaker operation. The linear timing marker output not only provides readable information concerning the refractory interval for each chamber, from cycle to cycle, but also enables distinguishing special pacer automatic modes of operation, such as the Wenckebach or block modes of limiting the ventricular response to high atrial rates. The special communications mode, whereby a plurality of bytes of data are stored each pacer cycle and transmitted to the external apparatus during the next successive cycle, i.e. in batch form, enables a substantial savings in chip space, a reduction in circuit complexity, and an increase in reliability. As used herein, the term event data encompasses sensed natural events (e.g., atrial and ventricular heartbeats) as well as device-generated events (e.g., delivered stimuli pulses, pulse inhibitions, etc.). Additional events may be recorded and graphed within the scope of this invention.

We claim:

1. A pacemaker system comprising an implantable dual chamber pacemaker having means for sensing atrial and ventricular events and means for timing atrial and ventricular pacemaker operation, and external apparatus for storing data and displaying data, characterized by
said pacemaker having output means for cyclically outputting event and pacemaker timing data representative of a prior pacemaker interval;
said external apparatus having means for receiving and storing said outputted data in storage; and
graphic constructing means for constructing from said stored data a dual channel graphic output representative of both atrial and ventricular pacemaker timing and events for a plurality of pacemaker cycles, said graphic constructing means further comprising linear print means for printing linear symbols respectively representative of different sensing conditions, said linear symbols having lengths representative of the time durations of said sensing conditions.

2. The system as described in claim 1, wherein said output means operates each pacemaker cycle to output a plurality of bytes representing said timing and event data, said plurality of bytes being outputted substantially immediately following a predetermined event which terminates the preceding cycle.

3. The system as described in claim 2, wherein said output means comprises means for outputting event data representative of ventricular sense occurrences.

4. The system as described in claim 1, further comprising event symbol means for outputting symbols indicative of events and for positioning said symbols in time relationship to said linear symbols.

5. The system as described in claim 4, wherein said event symbol means comprises means for graphing symbols representative of A sense, V sense, A pace, V pace, double sense, and inhibition of synchronized V stimulus following an atrial sense or pace.

6. The system as described in claim 4, wherein said linear print means comprises means for printing linear symbols representative of atrial no sensing, relative sensing and absolute sensing.

7. The system as described in claim 1, wherein said graphic constructing means comprises means for generating additional timing data by timing the interval between each successive transmission of said plurality of bytes.

8. The system as described in claim 1, wherein said constructing means comprises storage means for storing said timing and event data continuously from cycle to cycle, and means for printing a predetermined plurality of cycles in graphic form upon operator demand.

9. The system as described in claim 8, wherein said storage means comprises means for continuously storing groups of data corresponding to the n most recent pacemaker cycles.

10. A method for generating a graphic marker channel representative of event and timing data corresponding to operation of an implanted cyclically operating device, said graphic marker channel being presented on at least one time axis, comprising
cyclically outputting event and timing data representative of a prior device cycle, each said outputting comprising transmitting a group of data bytes corresponding to said prior device cycle;
storing consecutive groups of bytes in external storage, each group representative of event and timing data outputted just after completion of a device interval; and constructing a graphic marker channel representation of a plurality of device cycles, said graphic representation being derived from said groups of bytes and including line symbols printed along said time axis, each said line symbol being representative of the time duration of an operating condition of said device.

11. The method as described in claim 10, wherein said device is a pacemaker, and comprising outputting a group of bytes following a selected occurrence of each pacemaker cycle.

12. The method as described in claim 10, wherein said device comprises a pacemaker, and wherein said step of constructing a graphic marker channel representation comprises producing said line symbols representative of the timing of the pacemaker refractory interval.

13. The method as described in claim 10, wherein said device comprises a dual chamber pacemaker, and comprising constructing atrial and ventricular marker channel graphic outputs, at least one of said channel outputs comprising refractory interval line symbols.

14. A pacemaker system comprising a pacemaker and external apparatus, the pacemaker and external apparatus having means for communicating therebetween, characterized by said pacemaker having means for transmitting event and pacemaker timing data to said external apparatus, and said external apparatus having linear graphic means for generating a continuous linear graphic timing display of pacemaker operation over a plurality of cycles, said linear display including line symbols having lengths representative of the time durations of pacemaker operating conditions, and symbol means for generating graphic symbols representative of events and for positioning said graphic symbols relative to said linear timing display in correspondence with the timing of said events.

15. The pacemaker system as described in claim 14, wherein said pacemaker comprises programmable mode means for selectively operating in a single chamber or dual chamber mode, and said linear graphic means has dual means for generating a linear graphic display corresponding to both atrial and ventricular pacemaker operation.

16. The pacemaker system as described in claim 14, wherein said pacemaker has means for collecting event and timing data each cycle and for transmitting said data in batch form following said each cycle.

17. A method for generating a linear graphic marker channel output representative of event and timing data corresponding to operation of an implanted cyclically operating pacemaker, said method being carried out by a pacemaker system including said implanted pacemaker and external apparatus, comprising transmitting event and pacemaker timing data from said pacemaker to said external apparatus, receiving said data at said external apparatus and generating a linear graphic timing display of the operation of said pacemaker over a plurality of cycles, said generating step including utilizing said received data and printing lines having lengths representative of periods of time of operation of said pacemaker.

18. The method as described in claim 17, wherein said generating comprises printing said timing display to represent events and pacemaker timing with respect to a time scale, and printing respective different line symbols representative of a plurality of respective identifiable portions of refractory intervals of said pacemaker, said line symbols having lengths with respect to said time scale representing the durations of said portions.

19. The method as described in claim 18, comprising printed evoked QRS response with respect to said time scale.

20. The method described in claim 18, wherein said generating step comprises generating solid lines representing absolute refractory periods.

21. The method as described in claim 17, wherein said generating step comprises printing closed linear extensions representing relative refractory periods.

22. The method as described in claim 17, comprising generating graphic symbols representative of said sensed events and positioning said graphic symbols relative to said linear graphic timing display in correspondence with the timing of said events.

23. The method as described in claim 17, wherein said step of printing lines includes printing linear refractory interval timing diagrams presenting continuous information concerning a sense condition in said pacemaker.

* * * * *